(12) United States Patent
Barak

(10) Patent No.: US 6,881,043 B2
(45) Date of Patent: Apr. 19, 2005

(54) INJECTION APPARATUS INCORPORATING CLAMPING AND SQUEEZING MEMBERS FOR PUMPING LIQUID THROUGH FLEXIBLE TUBING

(75) Inventor: Swi Barak, Caesarea (IL)

(73) Assignee: Medrad, Inc., Indianola, PA (US)

( * ) Notice: Subject to any disclaimer, the term of this patent is extended or adjusted under 35 U.S.C. 154(b) by 0 days.

(21) Appl. No.: 10/057,798

(22) Filed: Jan. 25, 2002

(65) Prior Publication Data

US 2002/0127114 A1 Sep. 12, 2002

(30) Foreign Application Priority Data

Jan. 28, 2001 (IL) ................................................ 141137

(51) Int. Cl.⁷ ................................................ F04B 43/08
(52) U.S. Cl. .............................. 417/477.3; 417/477.1; 417/476; 417/53
(58) Field of Search .................. 417/12, 42, 477.1, 417/477.3, 476, 474

(56) References Cited

U.S. PATENT DOCUMENTS

| | | | |
|---|---|---|---|
| 3,966,358 A | | 6/1976 | Heimes et al. |
| 4,255,088 A | | 3/1981 | Newton et al. |
| 4,277,226 A | * | 7/1981 | Archibald .................... 417/38 |
| 4,396,385 A | | 8/1983 | Kelly et al. |
| 4,457,751 A | | 7/1984 | Rodler |
| 4,460,535 A | | 7/1984 | Kitoh et al. |
| 4,617,014 A | * | 10/1986 | Cannon et al. ............... 604/67 |
| 4,690,673 A | * | 9/1987 | Bloomquist .................. 604/67 |
| 4,781,548 A | * | 11/1988 | Alderson et al. ............ 417/474 |
| 4,854,836 A | * | 8/1989 | Borsanyi .................... 417/474 |
| 4,954,812 A | | 9/1990 | Lebron |
| 4,966,579 A | | 10/1990 | Polaschegg |
| 5,018,945 A | * | 5/1991 | D'Silva ........................ 417/12 |
| 5,057,076 A | | 10/1991 | Polaschegg |
| 5,176,631 A | | 1/1993 | Koenig |
| 5,417,213 A | | 5/1995 | Prince |
| 5,429,602 A | | 7/1995 | Hauser |
| 5,439,451 A | | 8/1995 | Collinson et al. |
| 5,494,036 A | | 2/1996 | Uber, III et al. |
| 5,616,124 A | | 4/1997 | Hague et al. |
| 5,739,508 A | | 4/1998 | Uber, III |
| 5,807,322 A | | 9/1998 | Lindsey et al. |
| 5,827,223 A | * | 10/1998 | Butterfield .................... 604/65 |
| 5,853,397 A | | 12/1998 | Shemesh et al. |
| 6,064,797 A | * | 5/2000 | Crittendon et al. ........... 417/22 |
| 6,083,206 A | | 7/2000 | Molko |
| 6,106,249 A | | 8/2000 | Barak ......................... 417/474 |
| 6,106,502 A | | 8/2000 | Richmond |
| 6,203,528 B1 | | 3/2001 | Deckert et al. |
| 6,213,738 B1 | | 4/2001 | Danby et al. |
| 6,224,578 B1 | | 5/2001 | Davis et al. |
| 6,248,093 B1 | | 6/2001 | Moberg |
| 6,261,262 B1 | | 7/2001 | Briggs et al. |
| 2002/0177821 A1 | | 11/2002 | Barak |
| 2003/0014035 A1 | | 1/2003 | Trombley, III et al. |

FOREIGN PATENT DOCUMENTS

| | | |
|---|---|---|
| DE | 197 14 711 | 10/1998 |
| JP | HEI 7-178169 | 7/1995 |
| WO | WO 03/006101 | 1/2003 |

OTHER PUBLICATIONS

Keeler, E. K., et al., "Accessory Equipment Considerations With Respect to MRI Compatibility, " JMRI, 8:12–18 (1998).

(Continued)

Primary Examiner—Cheryl J. Tyler
Assistant Examiner—Timothy P. Solak
(74) Attorney, Agent, or Firm—Gregory L. Bradley

(57) ABSTRACT

A piston pump propels liquid through a lumen of a flexible tube segment. The pump includes a first tube clamping member, a first set of tube squeezing members, a second tube clamping member, a second set of tube squeezing members and a synchronizing arrangement for activating the members in a sequential order such that fluid in the tube is displaced in a downstream direction.

35 Claims, 4 Drawing Sheets

OTHER PUBLICATIONS

Lemieux, L., et al., "Recording of EEG During fMRI Experiments: Patient Safety," MRM, 38:943–952 (1997).

Lemieux, L., et al., "Methodological Issues in EEG–Correlated Functional MRI Experiments," International Journal of Bioelectromagnetism, vol. 1, No. 1, p. 87–95 (1999).

"A Primer on Medical Device Interactions with Magnetic Resonance Imaging Systems," U.S. Food and Drug Administration, Center for Devices and Radiological Health (Feb. 7, 1997).

BodyGuard Operator's Manual, Version 06, Caesarea Medical Electronics, Ltd., Israel (May 2001).

BodyGuard Ambulatory Infusion Pump Product Brochure, Caesarea Medical Electronics, Ltd., Israel (no date).

Israeli Patent Application Serial No. 142446 filed Apr. 4, 2001, "A Flow Set and a Method to Identify Said Flow Set by a Liquid Pump," Caesarea Medical Electronics, Ltd., Israel.

Israeli Patent Application Serial No. 141137 filed Jan. 28, 2001, "Liquid Pump," Caesarea Medical Electronics, Ltd., Israel.

BodySet, IV Administration Set with Anti–siphon Valve, Male Luer Lock, CE0483, Manufactured by Teva Medical Ltd. for Caesarea Medical Electronics, Ltd., Israel (May 2001).

* cited by examiner

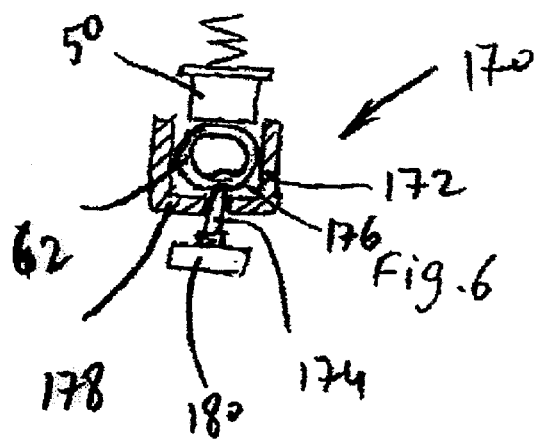
FIG. 4
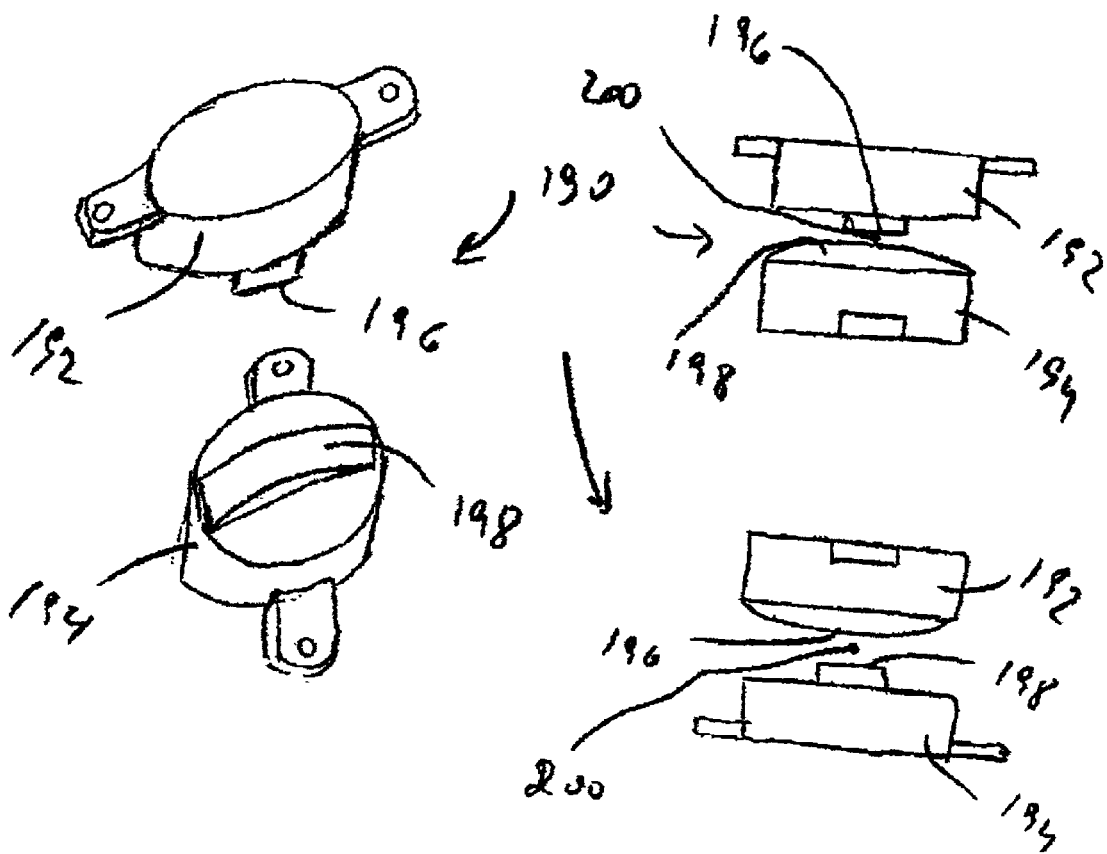
FIG. 6A
FIG. 5
FIG. 6B

INJECTION APPARATUS INCORPORATING CLAMPING AND SQUEEZING MEMBERS FOR PUMPING LIQUID THROUGH FLEXIBLE TUBING

BACKGROUND OF THE INVENTION

This invention relates to pumps and, more specifically, to a piston pump for administering liquids to a patient through a flexible tube.

Systems for administering liquids to a patient are widely known. However, a variety of different pumps are available for propelling a liquid to a patient, which may differ, among others, in the manner and principle in which they operate.

The present invention is concerned, in preferred embodiments, with two aspects of a system for administering a liquid to a patient. In a first aspect, the invention provides a pumping mechanism for a pump of the aforementioned type. In a second aspect, the invention provides control sensors suitable for use with a high-precision, liquid administering pump.

SUMMARY OF THE INVENTION

The invention provides, by a first of its aspects, a piston pump for propelling liquid through a lumen of a flexible tube segment. The pump includes a first tube-clamping member, a first set of tube squeezing members, a second tube clamping member and a second set of tube squeezing members. The members are preferably arranged in a direction from upstream to downstream. Further, the pump includes a synchronizing arrangement for activating the members in a sequential order such that fluid in the tube is displaced in a downstream direction.

The sequential activating order of the elements ensures continuous and repeatable operation of the pump, and comprises the following steps:

(a) activating the second tube-clamping member into blocking the tube's lumen and the first tube-clamping member to open the tube's lumen;

(b) activating the second set of tube squeezing members to constrict the respective tube portion and the first set of tube squeezing members to allow expansion of the respective tube portion;

(c) activating the first tube-clamping member into blocking the tube's lumen;

(d) activating the second clamping member to open the tube's lumen, and the second set of tube squeezing members to allow expansion of the respective tube portion; and (e) activating the first set of tube squeezing members to constrict the respective tube portion.

It will be noted, however, that the alphabetic characters used to designate the steps are provided for convenience only and do not imply any particular order of performing the steps.

According to one preferred embodiment of the invention, the first clamping member, the second clamping member and squeezing members of the first and second set are axially displaced along an axis normal to a longitudinal axis of the lumen between an open and a blocked position. Optionally, the pressing surface of the squeezing members can be either flat or designed shaped for designed squeezing.

According to still a preferred embodiment, the sectional area of the first set of squeezing members is about twice that of the second set of squeezing members.

By an improved design of the pump, there is further provided a counter member associated with a door of the pump, wherein the first and second tube-clamping members clamp the tube against the counter member. Further, the pump includes a flexible cradle associated at least with the first and second tube-squeezing member. The flexible cradle supports the tube at least at the expanded position. At the expanded position of the first and second tube squeezing members, the tube is pressed between the cradle and the first and second tube squeezing members so as to assume its shape.

The synchronizing arrangement preferably comprises a cam and follower mechanism associated with each of the members, and a revolving axle extending parallel to the tube's lumen. According to one possible arrangement, there are a number of eccentric members mounted on the axle. The eccentric members are operable to engage the tube clamping and the tube squeezing members, respectively, for imparting reciprocal axial displacement to them in a direction normal to the longitudinal axis. Preferably, the eccentric members are normally biased to engage the tube.

By another preferred embodiment, the present invention includes a disposal flow set including a drip chamber, an administration tube, a valve and a number of squeezing segments. Each squeezing segment preferably includes a stopper in each end. The stoppers are used for locating the segment in the pumping unit. When a segment loses its flexibility, another segment can be used.

By another preferred embodiment, the present invention includes a motor for rotating the axis on which the cams are located.

According to a second aspect of the present invention, there is provided a motor and a micro-controller to control motor revolutions in order to achieve an improved linear delivery of the liquid and to prevent pulsation effects. The micro-controller controls motor revolutions by using the following algorithm:

(a) the motor revolution is divided into a number of steps;

(b) a controller rotates the motor, sequentially from first step to last step of each revolution, wherein each step or a group of steps has an individual speed and an individual pause time between steps or a group of steps;

(c) the liquid flow, in the output of the pump, in measured in each step and pause; and (d) calculating or changing the speed of each step and duration of each pause, to have the desired flow function.

The algorithm can be used sequentially during the pump work, or can be used for calibration to obtain a revolution function—speed and time for each step and pause—and then use the obtained function to revolve the motor in further work.

According to another aspect of the present invention, there is provided a sensor unit for sensing the presence of gas cavities in a liquid flowing through a lumen of a flexible tube segment. The sensor comprises a transmitter unit having an arced transmitter plate with an apex extending along a line defining a first axis and a receiver unit having an arced receiver plate with an apex extending along a line defining a second axis. The two plates are preferably oppositely arced with their apexes facing one another defining a sensing space between them, the first and the second axes being essentially perpendicular to one another. Typically and preferably, the sensor is ultrasonic.

By second preferred embodiment, the tube extends through the sensing space such that each of the arced transmitter plate and the arced receiver plate contacts the tube.

By another preferred embodiment, the present invention includes communication capability enabling it to use any communication infrastructure to deliver information and receive commands.

By another aspect, there is provided a dripping sensor for sensing and counting the drips inside the drip chamber.

By another aspect, there is provided a sensor unit for a pump adapted for determining the pressure of a liquid flowing within a flexible tube segment. The sensor comprises a tube receiving space formed by walls engaging at least a portion of the tube while it is received within the space. Preferably, a sensing member projects into the space for determining deformation-resistance of the tube.

Preferably, the sensing member comprises a plunger associated with a strain gage. The tube receiving space is defined, by a preferred embodiment, between four walls defining a rectangular shape, and the plunger projects through one of the walls. By one specific design, the tube receiving space is defined between two or more arced surfaces.

Preferably, at a non-pressurized state of the tube, there remains a known clearance between the walls of the tube receiving space and the tube, whilst the tube is also deformed by the plunger at a non-pressurized state thereof.

BRIEF DESCRIPTION OF THE DRAWINGS

In order to understand the invention and to see how it may be carried out in practice, a preferred embodiment will now be described, by way of non-limiting examples only, with reference to the accompanying drawings, in which:

FIG. 4 is a sectional view of a pressure-sensing unit for incorporation in a pump of the aforementioned type;

FIG. 5 is a perspective, exploded view of a gas detection sensor for use in a pump of the aforementioned type; and FIGS. 6A and 6B are side views of the device seen in FIG. 5 rotated by 90°.

DETAILED DESCRIPTION OF SPECIFIC EMBODIMENTS

Figure 1:
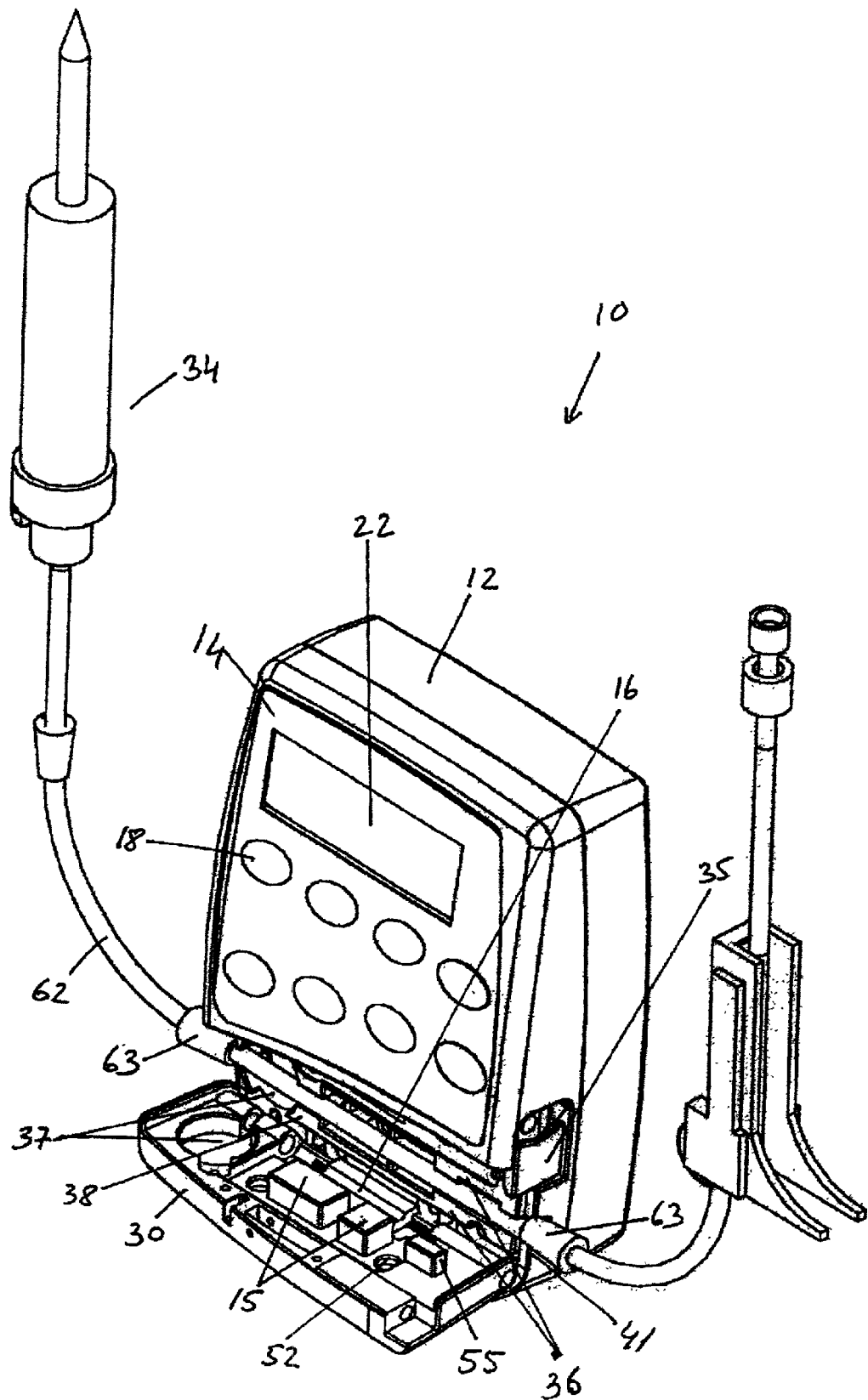
FIG. 1 is an isometric view of a pump in accordance with the present invention comprising a receptacle door being opened prior to engagement with a tube segment.

Reference is first made to FIG. 1, in which a piston pump (generally designated 10) is shown, comprising a housing 12, having a user interface unit 14 and a pumping assembly (generally designated 16). Typically, user interface 14 comprises a keypad 18, for input of data such as flow rate, flow time, etc., and to initiate or stop the pump, and a display 22.

The pumping assembly 16 comprises a door 30 pivotally engaged at pivots to a support structure of the pump (not shown). Door 30 comprises a release lever 35, a biasing spring (not shown) and an engaging hook portion 38 adapted for engagement with a corresponding lateral shoulder of a locking recess formed in the housing 12.

Door 30 carries also a counter member 15, which in the present embodiment is spring-biased by means of springs 52. The counter member 15 may be a rigid bar covered by a layer of flexible material, or it may also be made of a flexible material, e.g. a bar of silicon rubber, etc. The purpose of this counter member 15 will become apparent hereinafter.

The housing is formed with a receptacle 41 for receiving a segment—between two stoppers 63—of a flexible tube 62 of a flow set 34, such as of a drug administration set, etc. The receptacle 41 extends across the housing 12 between openings formed in the sidewalls of the housing 12. Receptacle 41 is also formed with two-well shaped portions and a major receptacle portion. It is further noted that the door 30 comprises a tube positioning extension 55 for depressing and positioning the tube 62 within the receptacle 41 at the openings of the housing. Furthermore, the receptacle may be provided with a micro switch (not shown) for generating a signal to the control unit of the pump, indicative of engagement of the pump with a segment of the tube. Suitable sensor means may also be provided to indicate proper closure of door 30. Two openings 37 are formed one in the door 30 and the other in the housing 12 to locate two parts of an air sensor. A pressure sensor 36 is located in the housing 12 between two sides of the tube 62.

Figure 2:
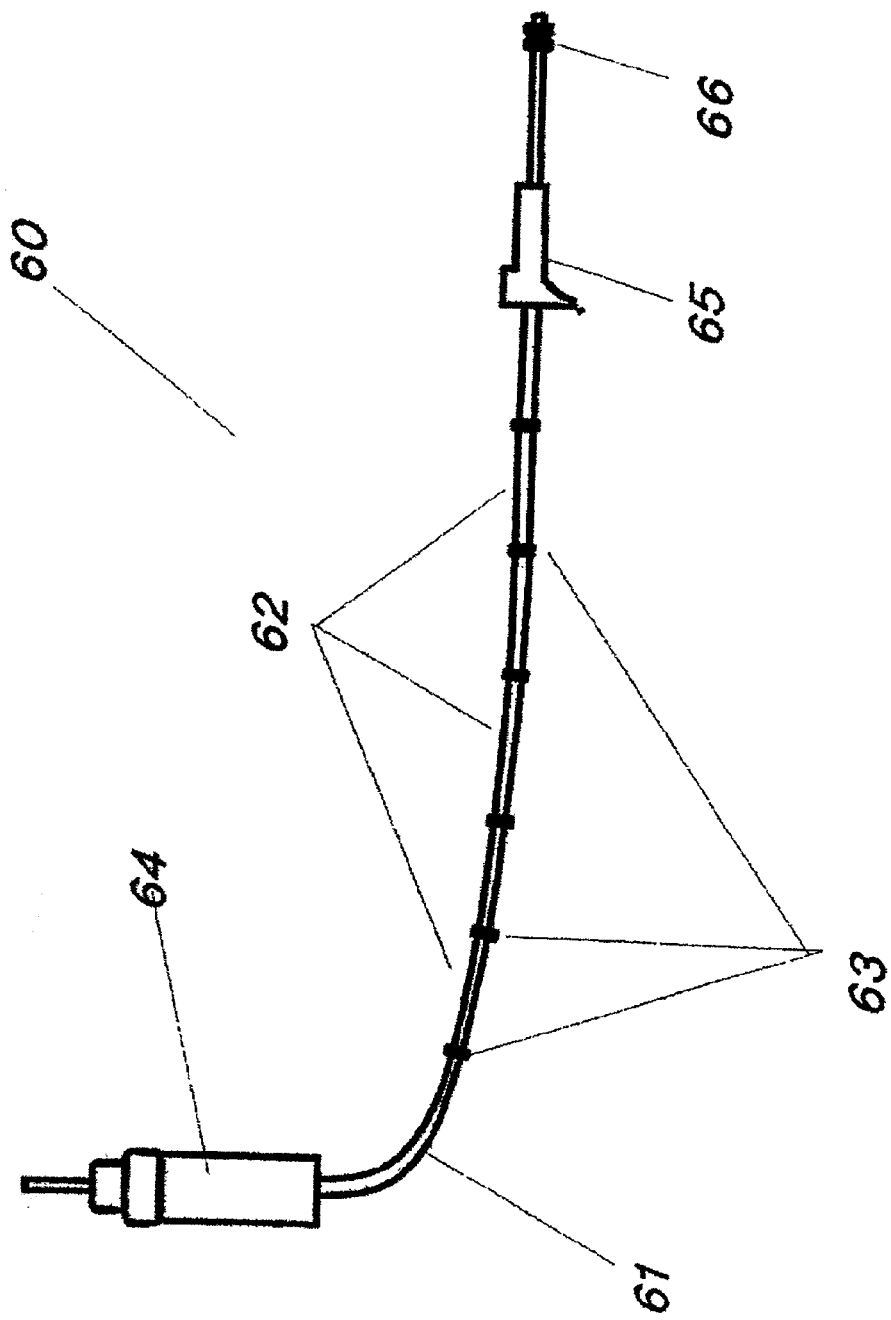
FIG. 2 is an illustration of a disposal flow set.
Figure 3A:
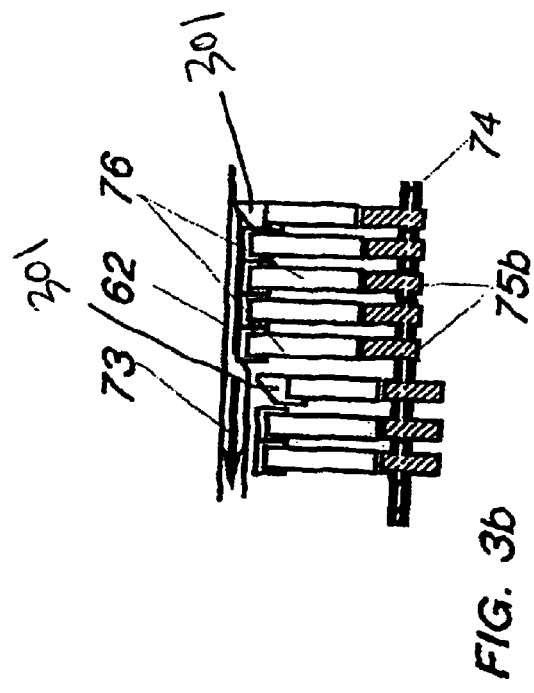
FIGS. 3a–3d show, in isolation, the piston mechanism, in continuous consecutive phases of the pump's operation.
Figure 3B:
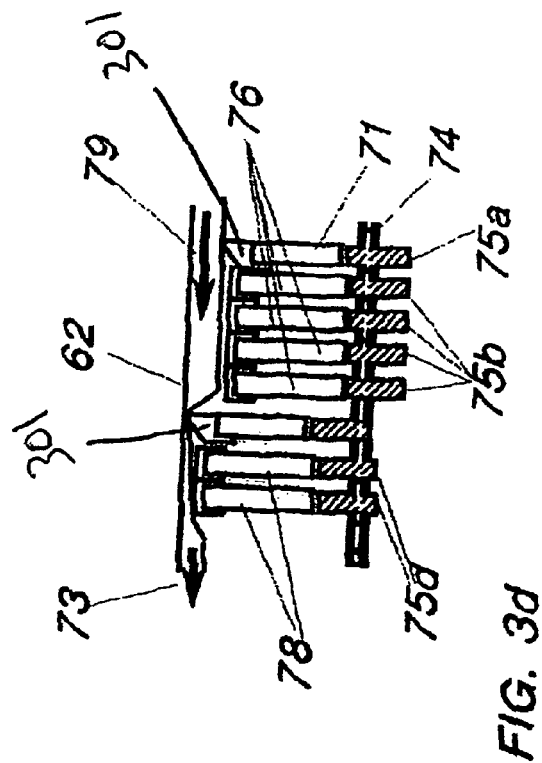
Figure 3C:
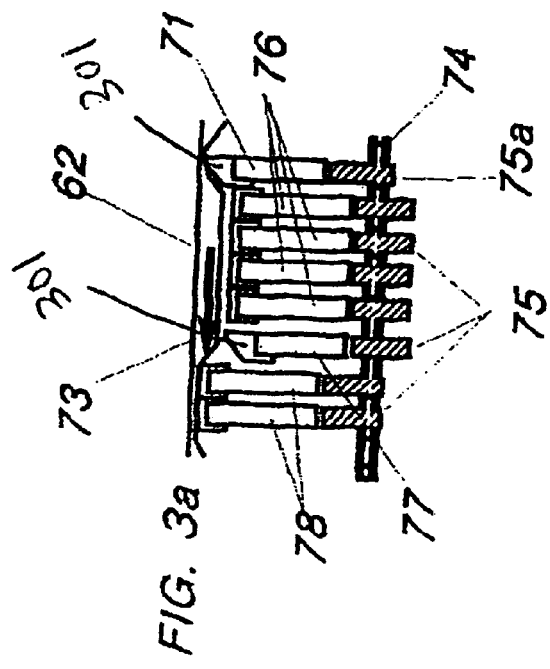
Figure 3D:
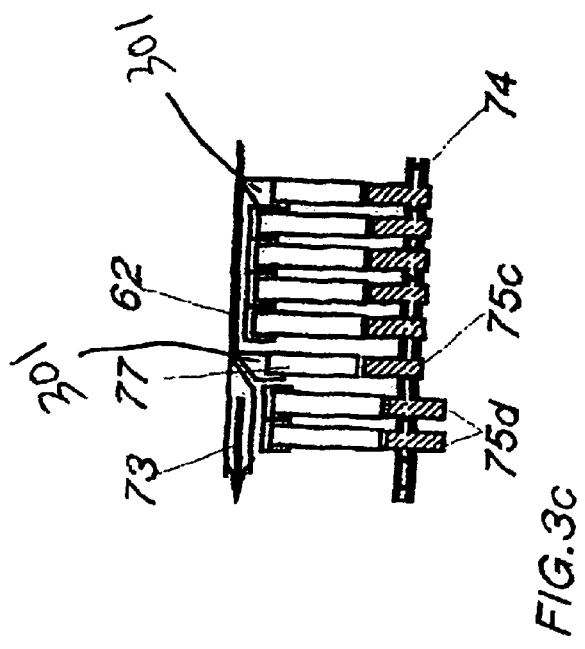

FIG. 2 illustrates a disposal flow set for use with the pump in order to administer a liquid. The flow set 60 includes an administration tube 61, which is separated into a number of pumping segments 62 wherein each segment is bordered by two stoppers 63. The stoppers 63 are used to locate one of the pumping segments in the pump, and when a segment loses its flexibility it can replaced by another segment. The flow set 60 includes a dripping chamber 64 that can be used for, inter alia, sensing and counting the drops passing through the chamber using a drip sensor (not shown). The flow set 60 includes a valve 65 and a connector 66 to connect the set to a patient.

FIGS. 3a–3d show, in isolation, the piston mechanism, in continuous consecutive phases of the pump's operation. The pump includes a first clamping member 71, a first set of squeezing members 76, a second clamping member 77, a second set of squeezing members 78, and an axis 74 with a number of eccentric cams 75 installed thereon to elevate and to lower each member according to the pumping sequence in order to clamp and squeeze a tube segment 62 to administer the liquid flow 73 from right to left.

In a first step, (FIG. 3a) the axis 74, with the eccentric cams 75, is revolved to a position that elevates the first clamping member 71 by an associated cam 75a, whereby the first clamping member clamps the right end of the tube segment 62 by means of blade surface 301. In a further stage of FIG. 3b, the axis 74 continues its revolution and the first set of squeezing members are elevated by associated cams 75b. The squeezing members 76 squeeze the tube segment 62 and force the liquid 73 to move left. In the next step (FIG. 3c), by the continuation of the revolution of the axis 74, the second clamping member 77 is elevated by an associated cam 75c and clamps the tube segment 62 in the left end of the squeezed area by means of blade surface 301. Meanwhile, the second squeezing set 78 is still elevated from the previous sequence, by the associated cams 75d, and starts to move down to ensure the continued flow of the liquid 73.

In the last sequential step (FIG. 3d), by the continuation of the axis 74 to revolve, the second set of squeezing members 78 are finished elevating and, in the meantime, the first set of squeezing members 76 and the first clamping member 71 are lowered by the associated cams 75a and 75b. While the remaining liquid 73 is pushed to the left, a new liquid 79 from a container (not shown) fills the right released part of the tube segment 62, ready for the next sequence of the pump when the second set of squeezing members 78 and the second clamping member 77 are lowered and the first clamping member 71 is elevated.

For best performance, preferably the squeezing size area of the first set of squeezing members 76 is about double the size of the squeezing size area of the second set of squeezing members 78, so as to ensure continuous propagation of liquid in a downward direction, where the volume of liquid received within the tube segment corresponding with the area of tube squeezing members 76 serves as a reservoir of liquid.

The cams are angularly diverted such that at least one or more of the cam followers constitute the first tube clamping member, one or more other cam followers constitute the second tube clamping member, several other cam followers arranged in the same orientation constitute the first set of tube squeezing members, and several other cam followers arranged in the same orientation constitute the second set of tube squeezing members.

Different parameters are maintained similar to the previous embodiment, e.g., the tube blocking cam followers engage the respective tube segment so as to essentially block the tube's lumen, whilst the tube squeezing cam followers engage the respective tube segment to only partially squeeze the tube's lumen. This may be achieved by differently forming the tube-engaging surface of the cam followers, or by shortening their lengths or by different forms of the cams.

In FIG. 4 of the drawings, there is illustrated the pressure sensing device 36 incorporated into the pump in accordance with the present invention, or other liquid administrating pump. The sensor unit 36 comprises a U-like receptacle 172 dimensioned so as to comfortably accommodate tube 62, with the counter member 55 closing the structure from above. A plunger 174 projects into the space 176 confined within the U-like receptacle 172 through a suitable opening at a bottom wall thereof 178 and is associated with a pressure sensing gauge 180, e.g. a piezo-electric gauge, string gauge, etc., for detecting pressure applied thereto by the tube 62, depending on its internal pressure applied by the liquid flowing through its lumen.

The arrangement of the sensor 36 ensures that local deformation of the tube is converted into terms of pressure without influence of overall deformation of the tube caused by the internal pressure of the liquid, this owing to the support walls of structure 172 preventing undesired deformation of the tube.

FIGS. 5 and 6 illustrate a sensor for detecting the presence of gas, typically air, flowing within the liquid carrying tube. The device (generally designated 190) is suitable for insertion within the openings 37 of housing 12 and comprises a transmitter unit 192 having an arced transmitter plate 196 and a receiver unit 194 having an arced receiver plate 198, with the two plates 196 and 198 being oppositely arced with their apexes facing one another defining between them a sensing space 200 (FIGS. 6A and 6B). In order to achieve sensing focus, the two plates 196 and 198 are preferably perpendicular to each other. Typically, the sensor is ultrasonic.

The arrangement is such that the entire cross-section of the tube is covered by the ultrasonic waves, thereby any air cavities, even if significantly small with respect to the cross-section of the tube, and even if not flowing axially centered within the tube, are detected.

Whilst preferred embodiments have been shown and described, it is to be understood that it is not intended thereby to limit the disclosure of the invention, but rather it is intended to cover all modifications and arrangements falling within the spirit and the scope of the invention, *mutatis mutandis*.

What is claimed is:

1. A pump for use with a flexible tube operably disposed therein for delivering liquid to a patient, the pump comprising:
   a first tube-clamping member having a range of motion to block the flexible tube;
   a first set of tube squeezing members, each of the first set of tube squeezing member having a range of motion limited to constrict the flexible tube;
   a second tube-clamping member having a range of motion to block the flexible tube;
   a second set of tube squeezing members, each of the second set of tube squeezing member having a range of motion limited to constrict the flexible tube, said first tube-clamping, first set of tube squeezing, second tube-clamping and second set of tube squeezing members being sequentially arranged in a direction from upstream to downstream;
   a motor; and
   a synchronizing device operably associated with said motor and said first tube-clamping, first set of tube squeezing, second tube-clamping and second set of tube squeezing members, said synchronizing device operable to activate said first tube-clamping, first set of tube squeezing, second tube-clamping and second set of tube squeezing members in a sequential order to engage the flexible tube such that liquid in the flexible tube is pumped in a downstream direction.

2. The pump of claim 1 wherein the flexible tube comprises a drip chamber, a valve, and at least one squeezing segment defining two ends, said tube-clamping and tube squeezing members being adapted to engage the at least one squeezing segment.

3. The pump of claim 2 wherein the flexible tube further comprises a drip sensor for sensing and counting the drips passing through said drip chamber.

4. The pump of claim 2 wherein each end of the at least one squeezing segment is associated with a stopper.

5. The pump of claim 1 wherein each member of said first and second set of tube squeezing members comprises a pressing surface adapted to constrict the flexible tube.

6. The pump of claim 1 wherein the squeezing area defined by said first set of squeezing members is about twice that of the squeezing area defined by said second set of squeezing members.

7. The pump of claim 1 wherein said synchronizing device comprises an axle and a plurality of eccentric cams operably associated with the axle, each of the plurality of cams adapted to engage a respective member of said clamping or squeezing members.

8. The pump of claim 7 wherein said motor is operable to revolve said synchronizing device.

9. The pump of claim 8, further comprising a controller for controlling said motor to achieve linear flow of liquid within the flexible tube, said controller using an algorithm for revolving said motor in a specific nonlinear revolution, the algorithm adapted to:
   divide the motor revolution into a number of steps;
   rotate said motor, sequentially from first step to the last step of each revolution, wherein each step or a group of steps has an individual speed and an individual pause time between steps or a group of steps;
   measure the liquid flow, in the output of the pump, in each step and in each pause;
   calculate or change the speed of each step and the duration of each pause, to achieve the desired flow function; and store an a memory the flow function of the nonlinear revolution of said motor.

10. The pump of claim 9, wherein said algorithm is used sequentially during the operation of the pump.

11. The pump of claim 10 wherein said algorithm is used for calibration to obtain said flow function of nonlinear revolution and said controller uses the obtained function to revolve said motor in further operation of the pump.

12. The pump of claim 1, further comprising an ultrasonic sensor operably associated with the flexible tube for detecting air therein.

13. The pump of claim 1, further comprising a communication device in communication with the motor and operable to deliver information and receive commands.

14. The pump of claim 1, further comprising a sensor unit adapted for determining the pressure of a liquid flowing within said flexible tube.

15. The pump of claim 14 wherein the sensor unit defines a tube receiving space formed by walls engaging at least a portion of said flexible tube and comprises a sensing member projecting into the space for determining deformation-resistance of said flexible tube.

16. The pump of claim 15 wherein said sensing member comprises a plunger associated with a strain gage, said tube receiving space is defined by a rectangular shape and said plunger projects through one of the walls defining said tube receiving space.

17. The pump of claim 1 wherein said first set of tube squeezing members comprises four tube squeezing members and said second set of tube squeezing members comprises two tube squeezing members.

18. The pump of claim 1 wherein each of said first and second tube-clamping members comprises a blade surface adapted to block the flexible tube.

19. A method for controlling a pump in which a flexible tube is disposed for delivery of a liquid, comprising:
   activating a second tube-clamping member into blocking a lumen of the tube and a first tube-clamping member to open the lumen of the tube;
   while the second tube clamping member blocks the lumen, activating a second set of tube squeezing members to constrict a second portion of the tube and a first set of tube squeezing members to allow expansion of a first portion of the tube;
   activating the first tube-clamping member into blocking the lumen of the tube;
   while the first tube-clamping member blocks the lumen, activating the second clamping member to open the lumen of the tube, and the second set of tube squeezing members to allow expansion of the second portion of the tube; and
   while the first tube-clamping member blocks the lumen and the second clamping member is not blocking the lumen and the second set of tube squeezing member are not constricting the lumen, activating the first set of tube squeezing members to constrict the first portion of the tube
   the first tube-clamping member being upstream from the first set of tube squeezing members, the first set of tube squeezing member being upstream from the second tube-clamping member, the second tube-clamping member being upstream from the second set of tube squeezing members.

20. An injection apparatus comprising, in combination, a pump for pumping liquid through a flexible tube;
   wherein the pump comprises:
   a motor;
   a first tube-clamping member having a range of motion to block the flexible tube;
   a first set of tube squeezing members, each of the first set of tube squeezing member having a range of motion limited to constrict the flexible tube;
   a second tub-clamping member having a range of motion to black the flexible tube;
   a second set of tube squeezing members, each of the second set of tube squeezing member having a range of motion limited to constrict the flexible tube, said first tube-clamping, first set of tube squeezing, second tube-clamping and second set of tube squeezing members being sequentially arranged in a direction from upstream to downstream; and
   a synchronizing device operably associated with said motor and said first tube-clamping, first set of tube squeezing, second tube-clamping and second set of tube squeezing members, said synchronizing device operable to activate said first tube-clamping, first set of tube squeezing, second tube-clamping and second set of tube squeezing members in a sequential order to engage the flexible tube such that fluid in the flexible tube is pumped in a downstream direction; and
   wherein the flexible tube comprises at least one squeezing segment operable to be engaged by said first tube-clamping, first set of tube squeezing, second tube-clamping and second set of tube squeezing members to pump fluid within the flexible tube in a downstream direction.

21. The injection apparatus of claim 20 wherein the squeezing area defined by said first set of squeezing members is about twice that of the squeezing area defined by said second set of squeezing area defined by said second set of squeezing members.

22. The injection apparatus of claim 20 wherein said synchronizing device comprises an axle and a plurality of eccentric cams operably associated with the axle, each of the plurality of cams adapted to engage a respective member of said clamping or squeezing members.

23. The injection apparatus of claim 20 wherein said first set of tube squeezing members comprises four tube squeezing members and said second set of tube squeezing members comprises two tube squeezing members.

24. The injection apparatus of claim 20 wherein each of said first and second tube-clamping members comprises a blade surface adapted to block the flexible tube.

25. An injection apparatus comprising a pump and a flexible tube for use with the pump, wherein the pump comprises:
   a first tube-clamping member having a range of motion to block the flexible tube;
   a first plurality of tube squeezing members, each of the second set of tube squeezing member having a range of motion limited to constrict the flexible tube;
   a second tube-clamping member having a range of motion to block the flexible tube; and
   a second plurality of tube squeezing members, each of the second set of tube squeezing member having a range of motion limited to constrict the flexible tube, said first tube-clamping, first plurality of tube squeezing, second tube-clamping and second plurality of tube squeezing members being sequentially arranged in a direction from upstream to downstream; and
   wherein the flexible tube comprises at least one squeezing segment operable to be engaged by said first tube-clamping, first plurality of tube squeezing, second tube-clamping and second plurality of tube squeezing members to pump fluid within the flexible tube in a downstream direction.

26. The injection apparatus of claim 25 wherein the pump further comprises a motor and a synchronizing device operably associated with said motor and said first tube-clamping, first plurality of tube squeezing, second tube-clamping and second plurality of tube squeezing members, said synchronizing device operable to activate said first tube-clamping, first plurality of tube squeezing, second tube-clamping and second plurality of tube squeezing members in a sequential order to engage the flexible tube such that fluid in the flexible tube is pumped in a downstream direction.

27. The injection apparatus of claim 26 wherein said synchronizing device comprises an axle and a plurality of eccentric cams operably associated with the axle, each of the plurality of cams adapted to engage a respective member of said clamping or squeezing members.

28. The injection apparatus of claim 25 wherein the squeezing area defined by said first plurality of squeezing members is about twice that of the squeezing area defined by said second plurality of squeezing members.

29. The injection apparatus of claim 25 wherein said first plurality of tube squeezing members comprises four tube squeezing members and said second plurality of tube squeezing members comprises two tube squeezing members.

30. The injection apparatus of claim 25 wherein each member of said first and second plurality of tube squeezing members comprises a pressing surface adapted to constrict the flexible tube.

31. The injection apparatus of claim 25 wherein each of said first and second tube-clamping members comprises a blade surface adapted to block the flexible tube.

32. A pump for use with a flexible tube operably disposed therein for delivering liquid to a patient, the pump comprising:
- a first tube-clamping member adapted to block the flexible tube;
- a first set of tube squeezing members adapted to constrict the flexible tube;
- a second tube-clamping member adapted to block the flexible tube;
- a second set of tube squeezing members adapted to constrict the flexible tube, said first tube-clamping, first set of tube squeezing, second tube-clamping and second met of tube squeezing members being sequentially arranged in a direction from upstream to downstream;
- a motor; and
- a synchronizing device operably associated with said motor and said first tube-clamping, clamping, first set of tube squeezing, second tube-clamping and second set of tube squeezing members, said synchronizing device operable to activate said first tube-clamping, first set of tube squeezing, second tube-clamping and second set of tube squeezing members in a sequential order to engage the flexible tube such that liquid in the flexible tube is pumped in a downstream direction; and
- a sensor unit adapted for determining the pressure of a liquid flowing within said flexible tube, the sensor unit defining a tube receiving space formed by walls engaging at least a portion of said flexible tube, the sensor comprising a sensing member projecting into the space for determining deformation-resistance of said flexible tub and a plunger associated with a strain gage, said tube receiving space being defined by a rectangular shape and said plunger projecting through one of the walls defining said tube receiving space.

33. A pump for use with a flexible tube operably disposed therein for delivering liquid to a patient, the pump comprising:
- a first tube-clamping member adapted having a range of motion to block the flexible tube;
- a first set of tube squeezing members adapted, each of the first set of tube squeezing member having a range of motion limited to constrict the flexible tube;
- a second tube-clamping member adapted having a range of motion to block the flexible tube;
- a second set of tube squeezing members adapted, each of the second set of tube squeezing member having a range of motion limited to constrict the flexible tube; said first tube-clamping, first set of tube squeezing, second tube-clamping and second set of tube squeezing members being sequentially arranged in a direction from upstream to downstream;
- a motor;
- a synchronizing device operably associated with said motor and said first tube-clamping, first set of tube squeezing, second tube-clamping and second set of tube squeezing members, said synchronizing device operable to activate said first tube-clamping, first set of tube squeezing, second tube-clamping and second set of tube squeezing members in a sequential order to engage the flexible tube such that liquid in the flexible tube is pumped in a downstream direction, said synchronizing device comprises an axle and a plurality of eccentric cams operably associated with the axle, each of the plurality of cams adapted to engage a respective member of said clamping or squeezing members, said motor being operable to revolve said synchronizing device; and
- a controller for controlling said motor to achieve linear flow of liquid within the flexible tube, said controller using an algorithm for revolving said motor in a specific nonlinear revolution, the algorithm adapted to:
    divide the motor revolution into a number of steps;
    rotate said motor, sequentially from first step to the last step of each revolution, wherein each step or a group of steps has an individual speed and an individual pause time between steps or a group of steps;
    measure the liquid flow, in the output of the pump, in each step mat in each pause;
    calculate or change the speed of each step and the duration of each pause, to achieve the desired flow function; and
    store in a memory the flow function of the nonlinear revolution of said motor.

34. The pump of claim 33 wherein said algorithm is used sequentially during the operation of the pump.

35. The pump of claim 34 wherein said algorithm is used for calibration to obtain said flow function of Monilinia revolution and said controller uses the obtained function to revolve said motor in further operation of the pump.

* * * * *